(12) United States Patent
Bershas

(10) Patent No.: US 6,329,206 B1
(45) Date of Patent: Dec. 11, 2001

(54) METHOD OF DETERMINING INHIBITOR CONCENTRATIONS IN INHIBITED ACIDIC PICKLING SOLUTIONS

(75) Inventor: James P. Bershas, West Bloomfield, MI (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/338,007

(22) Filed: Jun. 22, 1999

(51) Int. Cl.$^7$ ................................................. G01N 31/02
(52) U.S. Cl. ........................... 436/111; 436/73; 436/78; 436/84
(58) Field of Search ............................... 422/7, 12, 16, 422/84; 436/73, 78, 79, 111, 84; 252/387, 389.21

(56) References Cited

U.S. PATENT DOCUMENTS

| | | | |
|---|---|---|---|
| 3,728,421 | * | 4/1973 | Noothout ........................... 252/635 |
| 3,928,607 | * | 12/1975 | Luloff ............................... 106/18.31 |
| 4,129,448 | * | 12/1978 | Greenfield et al. ................ 442/124 |
| 4,511,658 | * | 4/1985 | Lambert et al. .................... 436/130 |
| 4,533,642 | * | 8/1985 | Kelly ................................. 436/78 |
| 4,765,958 | * | 8/1988 | Tygat et al. ........................ 422/12 |
| 5,242,893 | * | 9/1993 | Willingham ....................... 504/138 |

OTHER PUBLICATIONS

Rossmore and Sondossi "Advances in Applied Microbiology", 1988, 33, p. 230.*

Angyal, Organic Reactions, 1954, 8, p. 198.*

Gladych et al. in "Comprehensive Organic Chemistry", Ed. Sutherlans, Pergamon Press, v.2, 1979, p.90.*

Morrison and Boyd, Organic Chemistry, Allyn and Bacon, Inc., 1973, p. 633.*

Nicholls in "Comprehensive Inorganic Chemistry", Pergamon Press, 1973, vol. 3, 1009.*

Bottini et al. "2–Bromoallylamine", Org. Synth. Coll., v. V, 1973, p. 121.*

Angyal et al.,:The Sommelet Reaction. PArt V. N–Heteroaromatic aldehydes, J. Chem. Soc., 1953, p. 1740.*

\* cited by examiner

Primary Examiner—Jill Warden
Assistant Examiner—Yelena Gakh
(74) Attorney, Agent, or Firm—Wayne C. Jaeschke; Stephen D. Harper

(57) ABSTRACT

The concentration of a hexamethylenetetramine-containing inhibitor in an acid pickling solution that has accumulated dissolved iron from use of the solution in pickling ferriferous material can be estimated with sufficient accuracy for practical control of the pickling process by alkalinizing a sample of the pickling solution to a pH of at least 10.8, so that any iron content of the solution precipitates from the solution, separating the precipitate from the liquid remainder of the alkalinized sample, and determining by colorimetry the concentration in the liquid remainder of formaldehyde produced by acid catalyzed hydrolysis of the hexamethylenetetramine to formaldehyde and ammonia.

12 Claims, No Drawings

METHOD OF DETERMINING INHIBITOR CONCENTRATIONS IN INHIBITED ACIDIC PICKLING SOLUTIONS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to an analytical method for determining the concentration of an inhibitor that comprises hexamethylenetetramine in inhibited acidic pickling solutions. Hexamethylenetetramine, either alone or in combination with other inhibitors, is frequently present in such pickling solutions, which are widely used to pickle ferriferous metallic objects that have acquired scales or other bulk oxide containing layers during metallurgical processing. These inhibitors are generally used at relatively low concentrations in an aqueous pickling solution that also contains at least one strong mineral acid.

When the concentration of amine inhibitors in a pickling solution is sufficiently high, the pickling solution will dissolve all of the unwanted oxide layers from the surface of a ferriferous object while dissolving little or no iron from the metallic part of the object that underlies the unwanted oxide layers. However, if the concentration of inhibitor is too low, the pickling solution will rapidly dissolve the metallic part of a ferriferous object (unless the ferriferous object is made of an alloy that spontaneously passivates in the particular pickling solution being used). Such dissolution of the underlying metal is never desirable in a pickling process. Therefore, it is important to maintain the concentration of inhibitor at a sufficient level to prevent unwanted dissolution at all times during the process.

On the other hand, amine inhibitors are considerably more expensive than the other components of a pickling solution, and some mechanical loss of pickling solution is essentially inevitable in any practical pickling process, so that it is not economical to use a large excess of the inhibitor to avoid unwanted dissolution of the metallic parts of the object being pickled. Furthermore, even aside from mechanical losses, under many circumstances the concentration of effective amine inhibitors in a pickling solution will decrease during use or even storage of the pickling solution for reasons that are not fully understood. It is therefore advantageous to have a means of analytically determining the concentration of inhibitor(s) in a used pickling solution, in order to know whether more inhibitor needs to be added, and if so how much more, in order to maintain the action of the pickling solution at or near optimum.

It is relatively easy to determine the concentration of hexamethylenetetramine in a freshly made pickling solution. However, even optimal pickling solutions dissolve some iron from the scales they are intended to remove, and it has been found that dissolved iron often interferes with conventional analytical methods for hexamethylenetetramine. It is accordingly the major object of this invention to provide a method for analytically determining the concentration of hexamethylenetetramine in an acidic pickling solution that contains hexamethylenetetramine as an inhibitor, either alone or with other inhibitor substances, and also contains dissolved iron. Other alternative, concurrent, and/or subordinate objects will become apparent from the description below.

Except in the claims and the operating examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred, however. Also, throughout the description, unless expressly stated to the contrary: percent, "parts of", and ratio values are by weight or mass; the term "polymer" includes "oligomer", "copolymer", "terpolymer" and the like; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description or of generation in situ within the composition by chemical reaction(s) noted in the specification between one or more newly added constituents and one or more constituents already present in the composition when the other constituents are added, and does not preclude unspecified chemical interactions among the constituents of a mixture once mixed; specification of constituents in ionic form additionally implies the presence of sufficient counterions to produce electrical neutrality for the composition as a whole and for any substance added to the composition; any counterions thus implicitly specified preferably are selected from among other constituents explicitly specified in ionic form, to the extent possible; otherwise such counterions may be freely selected, except for avoiding counterions that act adversely to an object of the invention; the word "mole" means "gram mole", and the word itself and all of its grammatical variations may be used for any chemical species defined by all of the types and numbers of atoms present in it, irrespective of whether the species is ionic, neutral, unstable, hypothetical, or in fact a stable neutral substance with well defined molecules; the terms "solution", "soluble", "homogeneous", and the like are to be understood as including not only true equilibrium solutions or homogeneity but also dispersions that show no visually detectable tendency toward phase separation over a period of observation of at least 100, or preferably at least 1000, hours during which the material is mechanically undisturbed and the temperature of the material is maintained within the range of 18–25° C.; the first definition of an acronym or other abbreviation applies to all subsequent uses of the same acronym or other abbreviation; and the term "paint" and its grammatical variations includes all similar types of coatings that may be described by more specialized names such as "lacquer", "varnish", "primer coat", "top coat", "enamel", or the like.

BRIEF DESCRIPTION OF THE INVENTION

It has been found that the concentration of hexamethylenetetramine in a liquid aqueous pickling solution that has a pH value not more than 6.0 and that contains dissolved iron can be adequately determined by the following process operations:

(I) separating from the bulk of the pickling solution in which the concentration of hexamethylenetetramine is to be determined a first representative sample of said pickling solution, said first representative sample having a quantitatively known volume, mass, or both;

(II) alkalinizing said first representative sample by mixing therewith a sufficient amount of an alkalinizing agent and, optionally, additional water so as:

to raise the pH of the mixture of said first representative sample and said alkalinizing agent to a value of at least 10.8, whereby the iron content of said mixture is caused to precipitate as an iron containing solid from said mixture; and to bring the total volume, mass, or both of said mixture to a quantitatively known value;

(III) separating a second representative sample of the liquid portion of said mixture of said first representative sample and said alkalinizing agent from all of the solid portions of said mixture of said first representative sample and said alkalinizing agent;

(IV) determining the concentration of formaldehyde in said second representative sample; and (V) calculating the concentration of hexamethylenetetramine in said pickling solution from the value of the concentration of formaldehyde found in said second representative sample, assuming that:

each mole of hexamethylenetetramine in said first representative sample produces six moles of formaldehyde in said alkalinized mixture of said first representative sample and said alkalinizing agent; and all such produced formaldehyde remains dissolved in the liquid part of said alkalinized mixture.

When a mixture of hexamethylenetetramine and one or more other inhibitor substances is used as the inhibitor component in a pickling solution, the concentration of all the inhibitor substances can normally be measured with sufficient accuracy by measuring only the concentration of hexamethylenetetramine as described above and then calculating that any other inhibitor substance present in the used inhibited pickling solution is present in the same ratio to the hexamethylenetetramine that the other inhibitor substance had to hexamethylenetetramine in the inhibitor component of the pickling solution initially.

BRIEF DESCRIPTION OF THE SEVERAL VIEWS OF THE DRAWINGS

Not applicable.

DETAILED DESCRIPTION OF THE INVENTION AND ITS PREFERRED EMBODIMENTS

Ordinarily in a large scale pickling operation, concentrations per unit volume are preferred over concentrations per unit mass, because the volume of a large quantity of pickling solution is usually more easily measured with sufficient precision to determine whether the inhibitor concentration therein is within a good operating range. Therefore, in the remainder of the detailed discussion, it will be assumed that concentrations per unit volume are desired, but it will be apparent to those skilled in the art that the description could equally well apply, mutatis mutandis, if concentrations per unit mass were desired instead of or in addition to concentrations per unit volume.

The accuracy of the determination of concentration can not be greater than the accuracy within which the volume of the first representative sample is known. However, great accuracy is not normally needed in order to satisfy the purpose of this invention, because the minimum amount of inhibitor required for proper functioning is relatively small, so that it is not necessary to operate very close to this lower limit in order to achieve reasonable economy. Accordingly it is normally satisfactory and preferred that the value of the volume of the first representative sample be known quantitatively to such a degree that there is at least a 99% confidence level that any individual measured volume will differ from the true volume by an increment that is not more than, with increasing preference in the order given, 20, 15, 10, 8.0, 6.0, 4.0, or 2.0 percent of the measured volume. Such accuracy is readily achieved with conventional graduated laboratory volumetric glassware, the use of which is accordingly normally preferred.

For economy, the alkalinizing agent preferably is selected from alkali metal hydroxides, most preferably sodium hydroxide. Solid alkalinizing agents that are soluble in water can be used, but for convenience, a solution in water of the alkalinizing agent is generally preferred. In order to avoid dilution that would reduce the accuracy of the ultimate formaldehyde determination in operation (V), the concentration of the alkalinizing agent in the solution used in operation (II) of a method according to the invention preferably is at least, with increasing preference in the order given, 0.5, 0.8, 1.5, 2.0, 2.5, 3.0, 3.5, 4.0, 4.5, 5.0, 5.5, or 6.0 moles per kilogram of the total solution of the alkalinizing agent in water (this unit of concentration being hereinafter usually abbreviated as "M/kg")

The pH value for the second representative sample obtained in operation (III) of a method according to the invention as described above preferably is at least, with increasing preference in the order given, 11.00, 11.10, 11.20, 11.30, 11.40, or 11.50. If a pH value of at least 10.8 is not achieved, more alkalinizing agent should be added during operation (II) of a process according to the invention as described above, starting with a new, replicate first representative sample in operation (I) according to the invention as described above.

The hydrolysis of hexamethylenetetramine to formaldehyde and ammonia is acid catalyzed and favored by heating above normal ambient temperature. When a determination according to the method of this invention is made for a used inhibited pickling solution in which the inhibitor has been present together with the acid in the pickling solution and this solution has been at a temperature of at least 65° C. for at least thirty minutes before the sample is taken, no additional heating is needed in operation (II). If for any reason, the method according to the invention is to be used for a solution in which the inhibitor and acid have been mixed within the previous few minutes and/or have not been heated together above normal ambient temperature, the first representative sample should be heated to at least 65° C. and maintained at that temperature for at least thirty minutes before the alkalinization of operation (II) is begun.

The separation of a second representative sample of the liquid part of the mixture formed by the first representative sample, the alkalinizing agent, and any water added in addition to the first two materials noted may be accomplished by any suitable method such as centrifugation or filtration, with the latter normally preferred for convenience. Any suitable filtering medium may be used, with paper normally the most convenient. There is a slight preference for a filter paper conventionally designated as "slow", such as Whatman's #5, but almost any conventional laboratory filter paper appears to give adequate results in most instances. Sintered glass or ceramic filters are also effective but less convenient, because the precipitate formed is often gelatinous and correspondingly difficult to remove from non-disposable filter media.

The analytical determination of formaldehyde concentration in operation (IV) of a method according to the invention can be made by any suitable method, including several known per se in the prior art. For convenience and economy and in view of the relatively low precision needed, a colorimetric method based on reaction of formaldehyde with some other substance to form a colored product is normally preferred. When, as is usual, the concentration of formaldehyde is expected to be within a range from 0.1 to 10 milligrams per liter in the second representative sample, a particularly preferred colorimetric method utilizes the color-generating reaction between formaldehyde and the reagent 4-amino-3-hydrazino-5-mercapto-1,2,4-triazole, usually referred to by the trademark "Purpald" registered for it by Aldrich Chemical Company, from which it is commercially available. The formaldehhyde concentration is measured colorimetrically after reaction of the formaldehyde with the Purpald® reagent and an oxidizing agent in higly alkaline solution is complete. Pre-measured solutions and apparatus for such measurements are commercially available from CHEMetrics, Inc., Calverton, Va. under their designations K-4203™ test kit, R-4203 Vacu-vial™ ampoules, R-4201™ Activator Solution, and R-4202™ Activator Solution. Directions for using these materials are available from the supplier, are illustrated in the examples below, and are preferably followed. The use of the color comparator provided with the test kit eliminates the need for a spectrophotometer and is therefore preferred for convenience, when the determination of formaldehyde does not need to be known with more than about 20% accuracy, as is usually sufficient for practical control of pickling operations.

The mathematical and stoichiometric principles for performing operation (V) according to the invention as described above will be apparent to those skilled in the art. As an example, if the concentration of formaldehyde is measured in parts per million by weight, this unit being hereinafter usually abbreviated as "ppm", then the concentration $C_h$ in ppm of hexamethylenetetramine in the pickling solution sampled in operation (I) will be given by the following equation:

$$C_h = \{(0.778)C_f V_m\}/V_s$$

wherein: 0.778 is a stoichiometric factor equal to the molecular weight of hexamethylenetetramine divided by six times the molecular weight of formaldehyde; $C_f$ is the concentration of formaldehyde in ppm in the second representative sample as determined in operation (IV) of a process according to the invention as described above; $V_m$ is the volume of the mixture formed by alkalinizing the first representative sample in operation (II) of a method according to the invention as described above; and $V_s$ is the volume of the first representative sample, in the same volume units as $V_m$.

The invention may be further appreciated by consideration of the following, non-limiting examples and comparison examples.

EXAMPLE AND COMPARISON EXAMPLE GROUP 1

For this group, solutions of a commercial inhibitor in 10% HCl solution in water were prepared with 0.0, 4.0, and 8.0% contents of iron cations (supplied to the solution as iron chloride salts). From the known composition of the inhibitor, it could be calculated that each solution contained hexamethylenetetramine stoichiometrically equivalent to 387 ppm of formaldehyde. In examples according to the invention, the solutions were analyzed by the procedural steps set forth between centered dashed lines immediately below.

1. Remove a volume of 2.0 milliliters of each mixture of acid and inhibitor as a sample and transfer the sample to a 100 milliliter beaker. (This may conveniently be done with a pipette, graduated syringe, or the like.)
2. Carefully add 25.0 milliliters of a solution in water containing 250 grams of NaOH per kilogram of solution to the beaker into which the sample was transferred in step 1. (Caution: There is an exothermic reaction.) Transfer the contents to a 50 milliliter graduated cylinder or other volumetric vessel with a 50 milliliters volume indicator. Rinse the sides of the beaker with about 10 milliliters of deionized water (this material being hereinafter usually abbreviated as "DI water") and add the rinse water to the contents of the graduated cylinder. Add DI water to the 50 milliliters mark, return the contents to the beaker, and carefully swirl to ensure good mixing.
3. Filter the solution from step 2 by gravity through Whatman #1 or #5 filter paper. Continue filtering until a minimum of 20 milliliters has been collected. Use the filtrate for the next step outlined below. The pH of the filtrate should be 10.8 or higher. Make sure the temperature of the filtrate is <38° C. If it is not, cool the sample below this temperature.
4. Fill the sample cup supplied with the CHEMetrics test kit to its 20 milliliters mark with the filtrate from above.
5. Add to the contents of the sample cup 6 drops of CHEMetrics A-4201 and stir briefly with the tip of a CHEMetrics ampoule.
6. Add 4 drops of CHEMetrics A-4202 to the mixture prepared in step 5 and stir briefly.
7. Place the ampoule, with its frangible tip pointed downward, into the sample cup with the frangible tip at or near the bottom of the cup. Then snap the tip by pressing the ampoule against the side of the cup. The partial vacuum inside the ampoule as supplied causes a predetermined amount of the liquid in the cup to be imbibed into the ampoule through its very narrow neck. (The narrowness and length of the neck that remains on the ampoule after its frangible tip has been broken allows the ampoule to be quickly inverted for mixing without losing any substantial fraction of the liquid contents inside the ampoule.)
8. Mix the contents of the ampoule by inverting and then reinverting the ampoule. Wipe any liquid from the exterior of the ampoule and allow the ampoule, with its contained sample inside, to sit for 12 minutes on the flat end of the ampoule. This ensures full color development.
9. Use the appropriate comparator to determine the formaldehyde concentration in the sample inside the ampoule.

First hold the high range comparator in a nearly horizontal position directly beneath a bright source of light. Place the ampoule from step 8 between the color standards of the comparator, with the long axis of the sample ampoule parallel to the long axes of the comparator tubes, and move the sample ampoule from left to right until the best color match is found. This determines the appropriate concentration range. (The comparator tubes are the same shape and size as the sample ampoule over most of its length below its neck.)

If the color in the sample ampoule appears to be lighter than the least strongly colored (1.0 ppm) comparator tube in the high range comparator, place the ampoule from step 8, flat end downward, into the center tube of the low range comparator supplied with the kit. Direct the top of the low range comparator up toward a source of bright light while viewing from the bottom. Rotate the comparator until the color standard below the ampoule matches. Read the activity off the comparator.

10. Multiply the reading obtained from the appropriate comparator in step 9 by 19.45 to obtain the hexamethylenetetramine concentration in the original mixture in ppm.

When this procedure, using eleven replicate samples for each solution, was applied to the three solutions of inhibitor and acid with varying amounts of iron ions as described above, results were obtained as shown in Table 1 below.

TABLE 1

| Percent of Iron in Solution | Results of Analysis, Formaldehyde Concentration | |
| --- | --- | --- |
| | Average | Standard Deviation |
| 0 | 348 | 34.2 |
| 4 | 363 | 30.8 |
| 8 | 358 | 21.5 |

When, in comparison examples, the procedure above was followed except for eliminating the addition of sodium hydroxide solution in step 2 and the filtration of step 3, addition of the reagents that should develop a color by reaction with formaldehyde in the later steps produces no evidence of the presence of formaldehyde.

EXAMPLE GROUP 2

For this group, solutions of inhibitor and acid as for Group 1 were made, but the solutions contained no iron and had varying amounts of inhibitor. The analytical method was the same as for Group 1. Results are shown in Table 2 below.

TABLE 2

| Concentration of Inhibitor, | Concentration of Formaldehyde in Final Analytical Sample | |
| --- | --- | --- |
| Percent by Volume | Calculated | Measured |
| 0.2 | 43.5 | 44.1 |
| 0.1 | 24.3 | 26.6 |
| 0.075 | 18.2 | 20.0 |
| 0.050 | 12.1 | 12.6 |

The invention claimed is:

1. A process for determining the concentration of an amine inhibitor component that includes hexamethylenetetramine in a liquid aqueous pickling solution that has a pH value not more than 6.0, the process comprising the following operations:

(I) separating a testing sample from the pickling solution in which the concentration of inhibitor is to be determined, the testing sample having a quantitatively known volume, mass, or both, and optionally preheated at at least 65° C. for at least 30 min to form formaldehyde;

(II) alkalinizing the testing sample, the testing sample being preheated at at least 65° C. for at least 30 min to form formaldehyde, by adding a sufficient amount of an alkalinizing agent to form formaldehyde and to define a mixture and, optionally, adding water, wherein the pH of the mixture of the testing sample and the alkalinizing agent is raised to a value of at least 10.8 to accurately determine the formation of formaldehyde, whereby an iron content of the mixture is caused to precipitate as a solid from the mixture;

(III) separating an alkanized sample of the liquid portion of the mixture of the sample and the alkalinizing agent from all of the solid portions of the mixture of the testing sample and the alkalinizing agent;

(IV) determining the concentration of formaldehyde in the alkanized sample; and (V) calculating the concentration of hexamethylenetetramine in the pickling solution from the value of the concentration of formaldehyde found in the alkanized sample, wherein each mole of hexamethylenetetramine in the testing sample produces six moles of formaldehyde in the alkalinized mixture of the testing sample and the alkalinizing agent and all such produced formaldehyde remains dissolved in the liquid part of the alkalinized mixture.

2. A method according to claim 1, wherein step (IV) is performed by causing the formaldehyde to react quantitatively to form a colored product and the concentration of the colored product is determined colorimetrically.

3. A method according to claim 2, wherein the formaldehyde is reacted with 4-amino-3-hydrazino-5-mercapto-1,2,4-triazole as part of step (IV).

4. A method according to claim 3, wherein the liquid aqueous pickling solution comprises a mineral acid and dissolved iron cations that have been introduced into the pickling solution by its use in pickling a ferriferous substrate.

5. A method according to claim 2, wherein the liquid aqueous pickling solution comprises a mineral acid and dissolved iron cations that have been introduced into the pickling solution by its use in pickling a ferriferous substrate.

6. A method according to claim 1, wherein the liquid aqueous pickling solution comprises a mineral acid and dissolved iron cations that have been introduced into the pickling solution by its use in pickling a ferriferous substrate.

7. A method according to claim 6, wherein in operation (II) the pH of the mixture of said first representative sample and said alkalinizing agent has a value of at least 11.5.

8. A method according to claim 5, wherein in operation (II) the pH of the mixture of said first representative sample and said alkalinizing agent has a value of at least 11.5.

9. A method according to claim 4, wherein in operation (II) the pH of the mixture of said first representative sample and said alkalinizing agent has a value of at least 11.5.

10. A method according to claim 3, wherein in operation (II) the pH of the mixture of said first representative sample and said alkalinizing agent has a value of at least 11.5.

11. A method according to claim 2, wherein in operation (II) the pH of the mixture of said first representative sample and said alkalinizing agent has a value of at least 11.5.

12. A method according to claim 1, wherein in operation (II) the pH of the mixture of said first representative sample and said alkalinizing agent has a value of at least 11.5.

* * * * *

UNITED STATES PATENT AND TRADEMARK OFFICE
CERTIFICATE OF CORRECTION

PATENT NO. : 6,329,206 B1  
DATED : December 11, 2001  
INVENTOR(S) : Bershas

It is certified that error appears in the above-identified patent and that said Letters Patent is hereby corrected as shown below:

<u>Column 8,</u>
Line 4, after "least" and before "10.8", insert -- about --.

Signed and Sealed this

Third Day of February, 2004

JON W. DUDAS
*Acting Director of the United States Patent and Trademark Office*